United States Patent [19]

Samaras et al.

[11] Patent Number: 5,069,214

[45] Date of Patent: Dec. 3, 1991

[54] FLASH REFLECTANCE OXIMETER

[75] Inventors: George M. Samaras, Columbia, Md.; Steven M. Falk, Washington, D.C.; Otis R. Blaumanis, Sparks, Md.

[73] Assignee: GMS Engineering Corporation, Columbia, Md.

[21] Appl. No.: 284,496

[22] Filed: Dec. 14, 1988

[51] Int. Cl.$^5$ .............................................. A61B 5/14
[52] U.S. Cl. .................................................. 128/633
[58] Field of Search ................ 128/633, 634, 665, 666

[56] References Cited

U.S. PATENT DOCUMENTS

| | | |
|---|---|---|
| 3,177,757 | 4/1965 | Polanyi . |
| 3,461,856 | 8/1969 | Polanyi . |
| 3,647,299 | 3/1972 | Lavallee . |
| 4,167,331 | 9/1979 | Nielsen . |
| 4,305,398 | 12/1981 | Sawa . |
| 4,447,150 | 5/1984 | Heinemann ......................... 356/41 |
| 4,453,218 | 6/1984 | Sperinde et al. . |
| 4,523,279 | 6/1985 | Sperinde et al. . |
| 4,586,513 | 5/1986 | Hamaguri ........................... 128/633 |
| 4,714,080 | 12/1987 | Edgar, Jr. et al. . |
| 4,759,369 | 7/1988 | Taylor . |
| 4,796,636 | 1/1989 | Branstetter et al. . |
| 4,832,484 | 5/1989 | Aoyagi et al. ....................... 128/633 |
| 4,880,304 | 11/1989 | Jaeb et al. .......................... 128/633 |
| 4,883,353 | 11/1989 | Hausman et al. ................... 128/633 |

OTHER PUBLICATIONS

"Noninvasive Pulse Oximetry Utilizing Skin Reflectance Photoplethysmography", Yitzhak Mendelson and Burt D. Ochs, IEEE Transactions on Biomedical Engineering, vol. 35, No. 10, Oct. 1988.

"Design and Evaluation of a New Reflectance Pulse Oximeter Sensor", Y. Mendelson, J. C. Kent, B. L. Yocum, and M. J. Birle, Medical Instrumentation, vol. 22, No. 4, Aug. 1988.

"Noninvasive Transcutaneous Monitoring of Arterial Blood Gases", Yitzhak Mendelson and Robert A. Peura, IEEE Transactions on Biomedical Engineering, vol. BME-31, No. 12, Dec. 1984.

Wood et al. [Photoelectric Determination of Arterial Oxygen Saturation in Man, J. Lab. Clin. Med., 34:387–401 (1949)].

Sutterer et al. [Calculation and Digital Display of Whole Blood Oxygen Saturation by Analog Techniques, IEEE Trans. BME, 16(2):116–122 (1969)].

Yoshiya et al. [Spectrophotometric Monitoring of Arterial Oxygen in the Fingertip, Med. & Biol. Eng. & Comput., 18:27–32 (1980)].

Primary Examiner—Kyle L. Howell
Assistant Examiner—John Hanley
Attorney, Agent, or Firm—Kerkam, Stowell, Kondracki & Clarke

[57] ABSTRACT

A small battery-operated oximeter noninvasively measures tissue oxygenation. This oximeter employs a high intensity, very short duration light pulse that penetrates clothing of a patient. A photodetector assembly of the oximeter is responsive to light reflected through clothing of the patient. The oximeter optically filters the reflected light. A ratio of the intensity of reflected red light to the intensity of reflected infrared light indicates tissue oxygenation of the patient.

3 Claims, 3 Drawing Sheets

VIEW A-A

VIEW B-B

VIEW C-C

FLASH REFLECTANCE OXIMETER

BACKGROUND OF THE INVENTION

Effective treatment of a patient during a medical emergency requires that care of the patient begin immediately at the scene of the emergency. However, before such care is administered to the patient, an assessment must be made of a patient's status. A patient's status is normally diagnosed by visual examination and measurement of one or more traditional vital signs to determine cardiovascular and pulmonary functions. Cardiovascular functions include blood pressure, heart rate, ECG, and capillary refill time. Pulmonary functions include respiration rate and respiration volume.

The speed of assessing a patient's status determines the immediacy and type of medical care for that patient, which, in turn, determines the ultimate survival of such a patient. In the case of multiple patients, the assessment of each patient's status determines the priority of care to be administered to any one of the multiple patients, but also causes a delay in the administration of care while identifying patients who do not require immediate care or are beyond medical help.

Tissue hypoxia is a major cause of morbidity and the ultimate cause of death in such patients. A primary cause of tissue hypoxia is a failure of peripheral oxygen delivery to the tissue of a patient. Oxygen delivery depends on the patient's external oxygen supply, pulmonary function, cardiac output, and the oxygen transport capacity of the patient's blood. The oxygen transport capacity of blood, in turn, depends upon the concentration of functioning hemoglobin and the affinity of the hemoglobin for oxygen. Traditionally, the delivery of oxygen to the tissue (tissue oxygenation or tissue perfusion) is determined with noninvasive vital signs measurements or from invasive blood sampling and analysis of blood gases. However, blood sampling and analysis is inappropriate at the scene of an emergency. Vital signs measurements, while appropriate for monitoring a patient at the scene of an emergency, is slow. Typically, such measurements are on the order of one to two minutes. Sensors must be applied, vital signs determined, and the sensors removed. With multiple patients and limited medical personnel, determining these measurements delays the onset of care to each patient.

The amount of oxygen available for peripheral tissue oxygenation is best indicated by the amount of oxygenated hemoglobin. Oximetry is a photometric technique for determining the percentage of hemoglobin which is oxygenated in a tissue sample, either in vitro or in situ. Oximetry relies on unique spectral characteristics of oxygenated and deoxygenated hemoglobin moieties.

Oximetry does not measure absolute hemoglobin concentration, but measures the relative amount of oxygenated hemoglobin. In the case of reduced hematocrit, oxygen extraction from the blood will be accelerated and thus arteriolar and capillary hemoglobin saturation will be reduced and the oximeter will indicate a low reading. Under these conditions the reading can underestimate the correct $SaO_2$ at values below 50% saturation, which is exacerbated by reduced hematocrit. However, the clinical meaning of such an underestimated reading is correct, because a percent saturation below 70% is outside of the normal clinical range and indicates life-threatening hypoxia. The oximeter will not overestimate $SaO_2$.

Oximetry can be implemented either in a transmission mode or in a reflectance mode. In transmission mode oximetry, a tissue sample is transilluminated and the intensity of specific wavelengths of light transmitted through the tissue sample is measured to determine the percentage of oxygenated hemoglobin. In reflectance mode oximetry, the tissue sample is illuminated and the intensity of specific wavelengths of backscattered light is measured to determine the percentage of oxygenated hemoglobin.

Wood et al. [Photoelectric Determination of Arterial Oxygen Saturation in Man, J. Lab. Clin. Med., 34:387–401 (1949)] were the first to develop a device for absolute $SaO_2$ measurement in vivo. Wood et al. developed a transmission mode ear oximeter using red and infrared light. This oximeter yielded results within a few percentage points of direct gaseometric analysis. However, fundamental problems exist with this approach, and with all later non-pulsatile, transmission oximeters. The procedure is slow (on the order of minutes), bloodless ear readings are required for correction of a nonhemoglobin-related transmission offset signal, and the pinna must be warmed to arterialize the blood.

Sutterer et al. [Calculation and Digital Display of Whole Blood Oxygen Saturation by Analog Techniques, IEEE Trans. BME, 16(2):116–122 (1969)] reported the development of a fully electronic analog system for immediate determination of oxygen saturation in whole blood. The system performed a double scale calculation, as described by Wood et al., using 650 nm red light and 800 nm infrared light. The system displayed an output as a logarithmic ratio after measurement of a saline blank and a whole blood sample.

The in vivo application of transmission oximeters has been impeded by non-specific absorption of red and infrared light, which causes major problems in the calibration of oximeters. In an attempt to overcome this problem, Merrick et al. [Continuous Non-invasive Measurements of Arterial Blood Oxygen Levels, Hewlett-Packard J., 28(2):2–9 (1976)] developed a multi-wavelength ear oximeter employing 8 suitably chosen wavelengths between 650 nm and 1050 nm to adequately resolve the difference in light absorption with sufficient accuracy to derive $SaO_2$. This device basically extracted the necessary information from the spectral signature of the transmitted light signal, but still required hyperthermal arterialization of the capillary blood in the ear. The oximeter measured $SaO_2$ within 95% confidence limits of ±4% when in the range of 65% to 100% saturation with a response time constant of 3 seconds. However, at saturation levels below 65%, the oximeter consistently under-estimated the $SaO_2$.

Yoshiya et al. [Spectrophotometric Monitoring of Arterial Oxygen Saturation in the Fingertip, Med. & Biol. Eng. & Comput., 18:27–32 (1980)] introduced a pulse oximeter, recognizing that the pulsatile nature of arterial blood flow could be employed to circumvent two fundamental problems (nonspecific absorption and the arterialization requirement) of transmission oximetry. Previous transmission oximeters had measured the total signal of transillumination without discriminating between an oscillatory component caused by arterial blood changes and the non-oscillatory component caused by non-arterial blood and tissues. In pulse oximetry, the non-oscillatory component is electronically discarded and only the oscillatory component is utilized to determine $SaO_2$.

For traditional, clinical applications, the conventional, transmission mode, pulse oximeter is one means of rapid, noninvasive, and continuous monitoring of peripheral tissue oxygenation. However, this technology is sorely inadequate for use at the scene of an emergency due to a minimum number of suitable measurement sites on the patient, the time required to affix sensors, the susceptibility to noise or vibration, patient motion, and the inability to operate through clothing.

Transmission mode pulse oximeters have other important limitations. Raised bilirubin concentration will cause under-reading of the true $SaO_2$ saturation, as it absorbs light in the wavelengths used. A pulsating arteriolar vascular bed is required. The device will fail under conditions of cardiac arrest, placement of sensors distal to an inflated tourniquet or blood pressure cuff, intense vasoconstriction (due to chemical agents or hypothermia) or severe hypovolemia. A site for transillumination is required for sensor placement and motion artifact occurs when moving patients.

Polanyi et al. [New Reflection Oximeter, Rev. Sci. Instr., 31(4):401–403 (1960) and In Vivo Oximeter with Fast Dynamic Response, Rev. Sci. Instr., 33:1050-1054 (1962)] reported a device for in vivo measurements using fiberoptics mounted on a cardiac catheter. Subsequently, recognizing the utility of the reflectance approach for in-dwelling catheters, a number of workers developed or evaluated devices for in vivo reflectance oximetry. However, this work centered on developing invasive, catheter-based, devices.

U.S. Pat. No. 4,714,080 to Edgar, Jr. et al. concerns a non-invasive optical oximeter. A tissue sample is illuminated with light at two wavelengths. A photodetector senses light reflected by the tissue sample and produces an output signal indicating oxygen saturation.

In contrast to transmission oximetry, reflectance oximetry does not require transillumination and, thus, there is no limitation regarding measurement sites. Reflectance oximeters work quite well except at low oxygen saturations and abnormal hematocrits (except for recent devices incorporating hematocrit correction). However, reflectance oximeters of the past have required the direct exposure of tissue of a patient to the oximeter. The presence of any material, such as clothing or a protective wrap, between the reflectance oximeter and the tissue of the patient prevented such an oximeter from indicating tissue oxygenation.

A need exists for a device that instantaneously and noninvasively assesses tissue oxygenation of a patient without requiring the removal of clothing or protective wraps from the patient.

SUMMARY OF THE INVENTION

The invention concerns an apparatus for indicating the oxygenation of a tissue sample. The apparatus comprises a means for producing light of an intensity capable of penetrating material adjacent the tissue sample, such that the light is reflected by the tissue sample back through the material. The apparatus also comprises a means for responding to the reflected light and for producing an output signal related to the oxygenation of the tissue sample.

One embodiment of the invention concerns a small, lightweight, battery-operated device which yields virtually instantaneous, noninvasive measurement of tissue oxygenation. The embodiment employs a high intensity, short duration light pulse that penetrates clothing of a patient. Reflected light is optically filtered, light intensity at specific wavelengths is measured, and the ratio of oxygenated hemoglobin to total hemoglobin is determined. This hemoglobin ratio indicates arterial blood gas oxygen saturation ($SaO_2$).

DESCRIPTION OF THE INVENTION

The validity of Beer's Law has been repeatedly invoked in the evaluation of oximetric devices. However, "Beer's Law is not applicable to problems involving the multiple scattering processes found in biological heterogeneous media", as stated by Longini et al. [A Note on the Theory of Backscattering of Light by Living Tissue, IEEE Trans. BME, 15(1):156-160 (1968)].

A number of theoretical explanations have been offered for optical phenomena occurring in biological media associated with oximetry. One explanation is the photon diffusion approach, which is derived from the generalized transport equation of radiative transfer theory. The basic differential equation describing optical propagation by diffusion is:

$$-D\nabla^2\psi(\rho)+\Sigma_a(\rho)=S(\rho)$$

where $\psi$ represents the scattered photon flux, S is the source function, D is the diffusion constant, and $\Sigma_a$ is the absorption coefficient. While formulated for isotropic scatterers, the formula can also be applied to anisotropic scatterers by appropriate modification of D, S, and $\Sigma a$. The detailed equations for reflected or backscattered fluxes are not given here. As observed by Steinke et al. [Role of Light Scattering in Whole Blood Oximetry, IEEE Trans. BME, 33(3):294-301 (1986)], the relationship between total scattering effects and percent saturation is approximately linear.

The inventors have developed a reflection mode oximetry technique for noninvasive in vivo use in light of this linear relationship. Furthermore, the inventors have found that $SaO_2$ is approximately linearly related to the ratio of intensities of reflected infrared and red light. This linear relationship is quite good in the 55% to 95% saturation range, which is the only range of clinical interest for use at the scene of an emergency. To circumvent the problems of nonspecific absorption and arterialization, the inventors use the ratio of the difference of two temporally successive measurements (the change in intensity of infrared and red light) to determine $SaO_2$. In this manner, an absolute determination of $SaO_2$ can be obtained at any number of reasonable sites on an individual and is not limited to fingers, toes, ears, or nose. Additionally, in order to penetrate clothing, a very high intensity light source is employed. To circumvent the potential problem of burning the patient, the duration of each illumination is kept extremely short. The duration of each illumination is basically a "flash" of light. The very high intensity, short duration light pulse dissipates the same energy as a low intensity, continuous light source. The inventors have recognized that, with the advent of high speed, low cost, miniature optical sensors, a new approach to noninvasive oximetry is possible.

Figure 1:
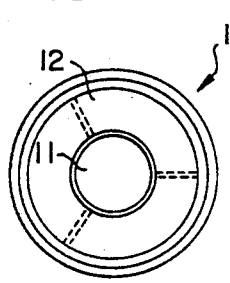
FIG. 1 shows a front view of a flash reflectance oximeter according to this invention.
Figure 2:
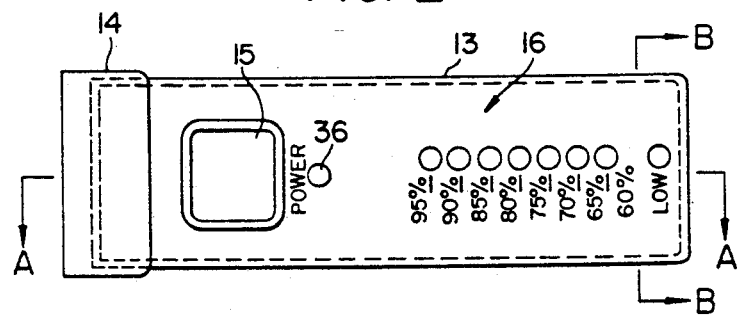
FIG. 2 shows a side view of the oximeter of FIG. 1.

FIG. 1 shows a front view of the reflectance oximeter 10 of this invention, including a lamp face 11 and an annulus 12 for receiving backscattered light. FIG. 2 shows a side view of the oximeter of FIG. 1. The cylindrical oximeter of FIGS. 1 and 2 comprises an aluminum housing 13, a sliding collar switch 14, power switch 15, and a visual display 16. In a preferred embodiment, the aluminum housing 13 is 2.18" by 7.0". The aluminum housing 13 contains optics, electronics on printed circuit boards, batteries, operator controls, visual display, and an electrical connector (for recharging batteries).

The visual display 16 comprises either a liquid crystal display (LCD) or light emitting diode (LED) display. A LCD is preferable to a LED display due to the dramatically lower power consumption requirements of the LCD display. Also, a LED display cannot be used in bright sunlight without shading (i.e., by hand). However, a LCD cannot be used in the dark and requires backlighting and more power consumption.

Figure 3:
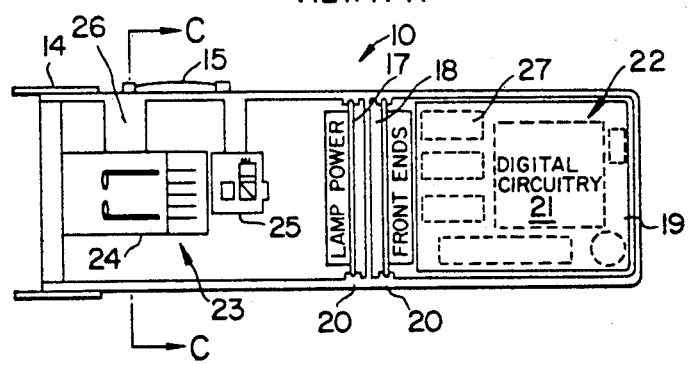
FIGS. 3, 4, and 5 show cutaway views of the oximeter of FIG. 1.

FIG. 3 is a sectional view through a cylindrical axis of the oximeter 10 at line A—A of FIG. 2 and is perpendicular to the view of FIG. 1. FIG. 3 shows the location of an optical assembly 23 and three printed circuit boards (lamp power circuit board 17, analog front ends circuit board 18, and digital circuit board 19). Integral mountings 20 are provided for the three printed circuit boards 17, 18, and 19. The analog front ends circuit boards 18 and digital circuit board 19 are mounted in a rear compartment 22. Digital electronics 21 on the digital circuit board 19 are shielded from the circuits of the analog front ends circuit board 18 to prevent electromagnetic interference with photodetectors and a microcomputer, described below. The optical assembly comprises a lamp assembly 24 and a detector/beam splitter assembly 25, which are each mounted on three struts located at 120 degree intervals. One mounting strut 26 of three is shown supporting the lamp assembly 24 and the detector/beam splitter assembly 25.

Figure 4:
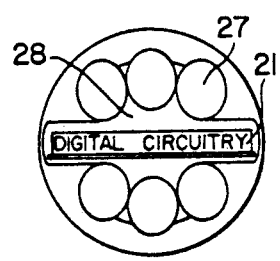

FIG. 4 shows a sectional view at line B—B of FIG. 2, and is perpendicular to the cylindrical axis. FIG. 4 shows the location of six batteries 27 and the digital circuitry 21. The batteries comprise six 1.2 VDC, 1000 mA-Hr NiCd cells, which are mounted in a compartment 28.

Figure 5:
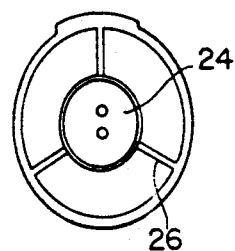

FIG. 5 shows a sectional view at line C—C of FIG. 3, also perpendicular to the cylindrical axis. FIG. 5 shows the location of the three mounting struts 26 for the lamp assembly 24.

Figure 6:
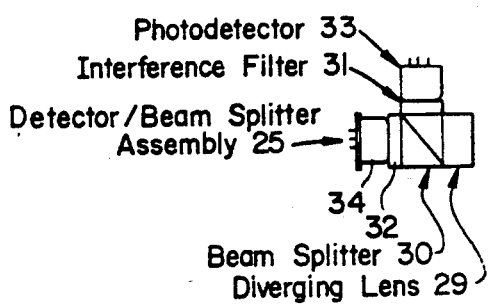
FIG. 6 shows an enlarged view of a detector and beam splitter assembly.

FIG. 6 shows an enlarged view of the detector/beam splitter assembly 25. The detector/beam splitter assembly 25 includes a diverging lens 29 that receives backscattered light. The diverging lens 29 transmits the light to a beam splitter 30 that directs the light to two interference filters 31 and 32. One filter passes red light to a first photodetector 33 and the other light passes infrared light to a second photodetector 34. The output of these photodetectors 33 and 34 represents the intensity of red light and the intensity of infrared light reflected back from the tissue of a patient when a high intensity, short duration pulse of light is directed toward the patient. These intensities are used in determining tissue oxygenation according to this invention.

Figure 7:
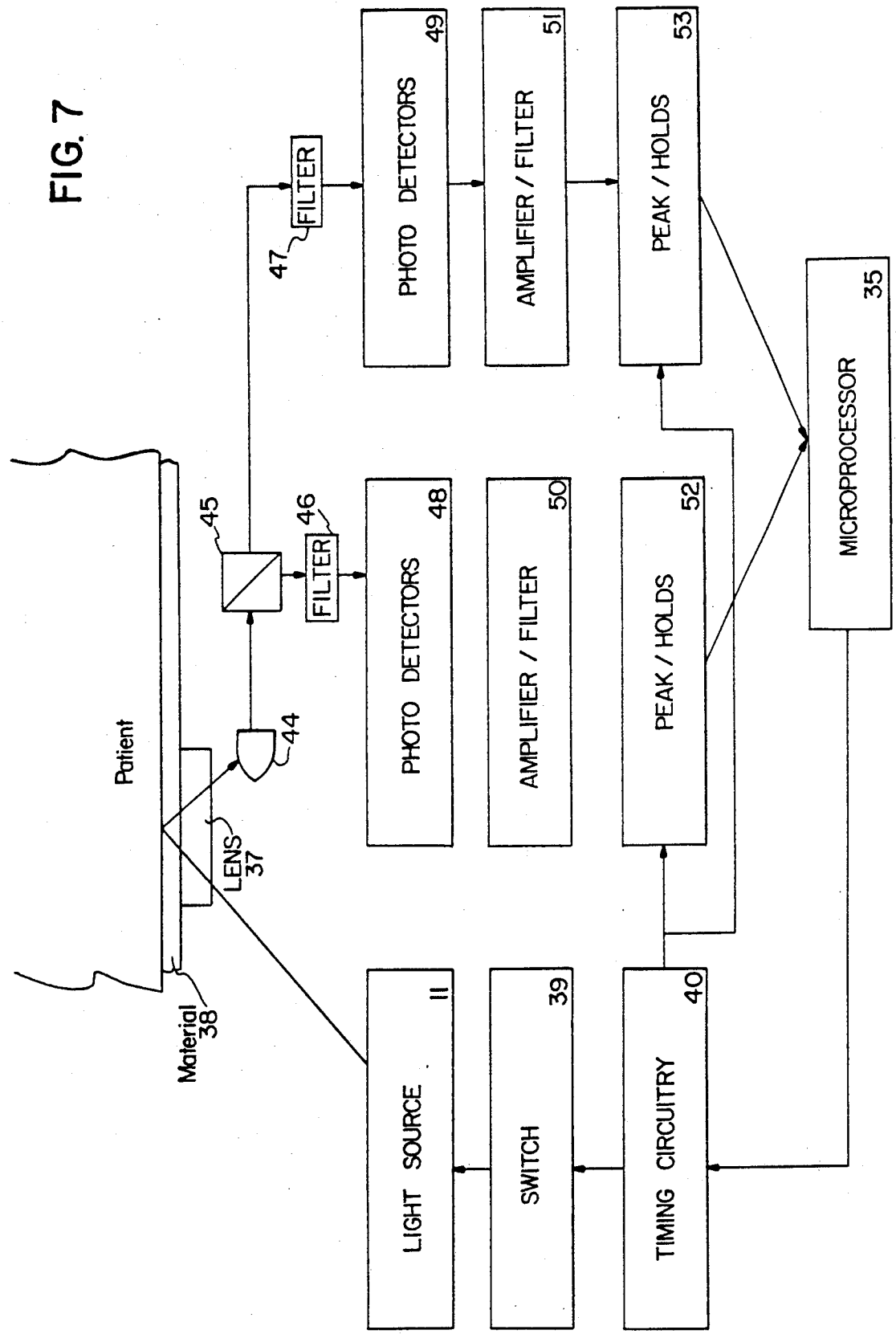
FIG. 7 is a block diagram illustrating the operation of the oximeter of this invention.

FIG. 7 is a block diagram illustrating the operation of the oximeter of this invention. When the power switch 15 is actuated, a microcomputer 35 executes a setup sequence for an $SaO_2$ measurement, enables lamp power circuity, enables a power indicator light 36 of FIG. 1, and retires to a low power consumption mode until either one minute has elapsed (in which case all power to the device is removed to conserve the battery) or until the sliding collar switch 14 is actuated by pushing the oximeter 10 onto a patient. Once the sliding collar switch 14 is actuated, the unit executes a series of four (2 $\mu$sec duration) lamp flashes over a 750 msec period, for instance. Between successive flashes, the microcomputer 35 retires to a low power consumption mode to conserve power.

Each flash of light from a light source, encased in a collimating shell, is directed through a converging, infrared-grade lens 37 in contact with material comprising clothing or protective wraps on the patient. The flash of light passes through the material 38, reflects off the patient, and passes back through the material 38 to a photodetector of this invention. The light source requires a high voltage, ultra-low current power, derived from the batteries 27 using a switch 39 and timing circuitry 40.

A converging lens 37 captures the backscattered light and directs the light to a metallized glass parabolic reflector 44. The parabolic reflector 44 directs this light to a diverging lens 29 of the beam splitter assembly 25. Two beams of light emanate from the diverging lens 29, are filtered by narrow bandwidth optical filters 46 and 47 (670 and 905 nm with 10 nm half-bandwidths, for instance), and illuminate high-speed light detectors comprising red and infrared photodiodes 48 and 49. The output of each of the red and infrared light photodiodes 48 and 49 is amplified and electronically filtered by amplifier/filter circuits 50 and 51. The output of each amplifier/filter circuit 50 and 51 is directed to an electronically resetable, analog peak-holds circuit 52 and 53. Each analog peak-holds circuit 52 or 53 holds a maximum output signal from corresponding photodiode 48 or 49 until the peak-holds circuit 52 or 53 is reset. The ratio of these two held signals (corresponding to oxygenated hemoglobin and total hemoglobin) is proportional to the normalized oxygen saturation level of the tissue interrogated, and is available less than one millisecond after the flash lamp is triggered. Detector circuitry is properly synchronized, so the resulting reflected or backscattered light peak can be captured.

The oximeter produces four flashes. After the fourth flash and digitization, six differences are mathematically examined by a microcomputer 35 to derive the largest difference of intensity of the red light channel and the largest difference of intensity of the infrared channel. From the last three measured differences of the red channel ($R_2-R_1$; $R_3-R_1$; $R_4-R_1$), all six possible differences ($R_2-R_1$; $R_3-R_1$; $R_4-R_1$; $R_3-R_2$; $R_4-R_2$; $R_4-R_3$) can be mathematically developed for the red channel. The same can be accomplished for the infrared channel. The first measurement on each channel ($R_1-R_1$ and $IR_1-IR_1$) permits real-time compensation of imbalances in the analog front ends. It is not necessary to determine the pulse amplitude, but to determine a reasonable difference in the oscillating component to obtain an adequate signal to noise ratio. Over the range of 30 to 180 bpm pulse rate (half-periods of 167 to 1000 msec), a properly sequenced series of flashes yield the desired differences.

Once red $I_r$ and infrared $I_{ir}$ light differences have been selected, SaO$_2$ is determined by the following formula:

$$SaO_2 = A - B \{\Delta[I_{ir}]/\Delta[I_r]\}$$

where A and B are constants dependent upon the instrument design and independent of the patient under interrogation. This equation for determining SaO$_2$ has not been corrected for altitude, for simplicity. The computed SaO$_2$, expressed as a percentage, is displayed in increments of 5.0 percentage points over the range of 60% to 95%. Other display formats can be implemented.

The operator of this oximeter 10 can command the microcomputer 35 to adjust the intensity and duration of each flash. An operator in a cold climate can command the microcomputer 35 to increase the intensity of each flash to penetrate thick layers of clothing or material 38. An operator in a warm climate can command the microcomputer 35 to decrease the intensity of each flash to penetrate thin layers of clothing or to reflect directly off exposed skin. The microcomputer 35 adjusts the duration of a flash to less than 200 nsec or more than 10 μsec according to changes in the intensity of the flash.

In a preferred embodiment, the circuitry of this invention comprises high amplitude, ultra-fast components to handle 4 or 5 pulses in one second; each pulse from 200 ns to 10 μs long. As used herein, "high speed" refers to a component which is responsive to, or capable of producing, a pulse of having a width which is sufficiently small to avoid burning a patient's skin when the pulse intensity is sufficiently high to allow measurements through clothing. A low power CMOS single chip microcomputer 35 comprises a single 68 pin PGA package, central processing unit, RAM, ROM, multiplex analog-to-digital converter, digital input and output, and timers. The microcomputer 35 drives the visual display 16 (LED or LCD), controls the peak-holds circuits 52 and 53 and the lamp timing circuitry 40. The light source 11 comprises a light emitting diode which can be driven with high power for a short time. A high speed timing circuit 39 and 40 to switch the lamp comprises a high speed buffer amplifier and a switching transistor. A high speed detector circuit comprises photodiodes 48 and 49 (PIN Photodiodes) or a Photodiode with Operational Amplifier which are very sensitive to photons. The high speed detector circuit also comprises a wide-bandwidth amplifier having a fast response time to see fast signals.

Figure 8:
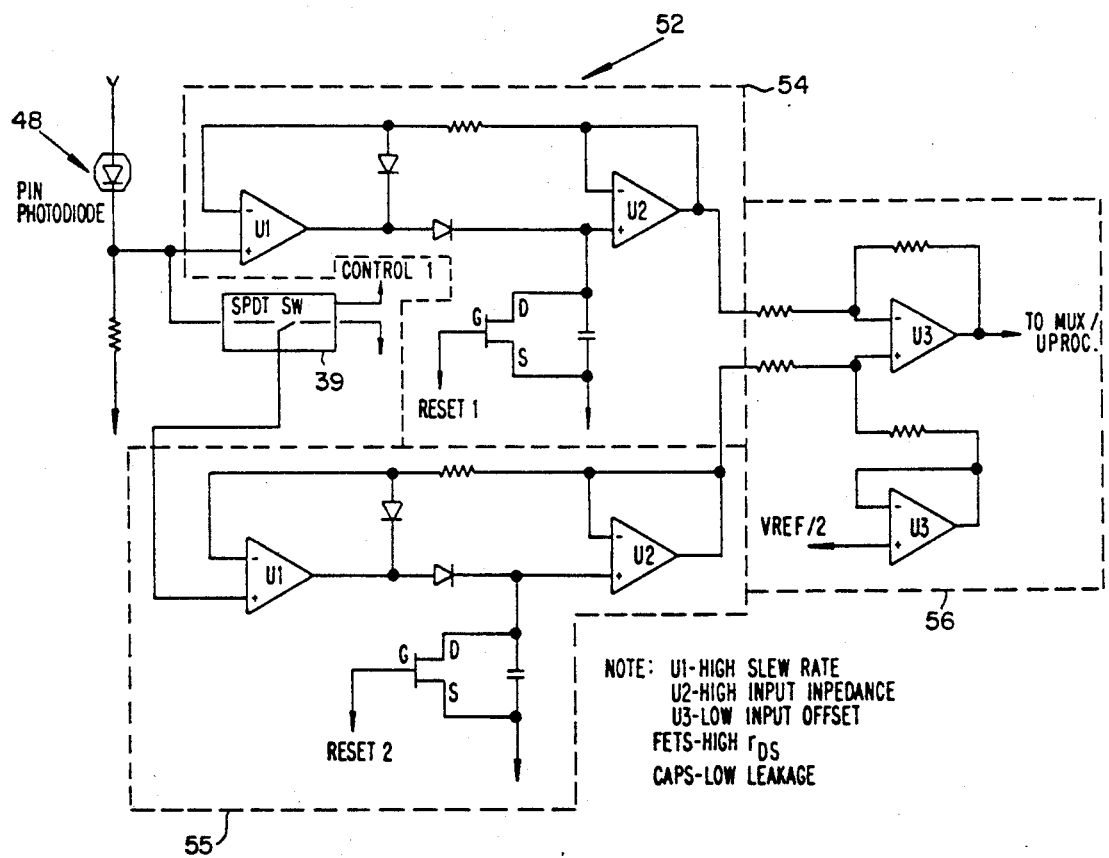
FIG. 8 is a schematic diagram illustrating an analog front end of this invention.

FIG. 8 is a schematic diagram illustrating a front end analog circuit for photodiode 48, it being understood from FIG. 7 that an identical circuit is used for photodiode 49. The front end analog circuit receives timing signals at RESET 1 and RESET 2 from the timing circuitry 40. The front end analog circuit comprises the circuit switch 39, one peak-holds circuit 52, and one photodetector 48 or 49 of FIG. 7. During the first flash, both peak-hold channels 54 and 55, of peak-holds circuit 52, are connected to the photodiode 48. The resulting output of each peak-hold channel 54 and 55 is the same. As a result, the output of a differential amplifier 56 connected to both peak-hold channels 54 and 55 is zero, indicating that the front end analog circuit is balanced. The switch 39 then opens the peak-hold channel 55 from the photodetector 48, such that, during the three subsequent flashes, only the peak-hold channel 54 is connected to the photodiode 48. The peak-hold channel 55 continues to hold the signal corresponding to $R_1$, whereas channel 54 holds $R_2$, $R_3$, and $R_4$ upon the second, third and fourth pulses, which allows differential amplifier 56 to produce $R_2 - R_1$; $R_3 - R_1$; and $R_4 - R_1$. These three signals may be used to derive the signals or differences of $R_3 - R_2$; $R_4 - R_2$; and $R_4 - R_3$ in the microprocessor 35 such that the microprocessor has all six possible differences as discussed concerning FIG. 7 above. This approach effectively increases the dynamic range of the measurement, by automatically eliminating the non-oscillatory component of the signal. This approach also eliminates part of the oscillatory component, which can be mathematically recovered from the set of four sequential measurements.

To obtain an accurate (though not absolute) ratio, the gain of each of two such channels is balanced to compensate for variations in the beam splitter assembly 45, the relative optical attenuation of the filters 46 and 47, the spectral distribution of the lamp 11 output, photodetector 48 and 49 imbalances, and gain differences in the electronics. This is accomplished by trimming a final stage difference amplifier and attenuator on each front end analog circuit.

The flash reflectance oximeter does not necessarily require a microcomputer 35. Dedicated analog and digital circuitry can be designed. However, it is significantly easier to reconfigure a microcomputer-based device by changing the software than to repeatedly redesign high speed analog and digital logic circuitry, with all the attendant noise and printed circuit board design problems. Therefore, to simplify development, a microcomputer has been employed.

Since SaO$_2$ varies as a function of pressure, a temperature compensated pressure transducer can measure barometric pressure to compensate for changes in SaO$_2$ due to changes in altitude. A conventional pressure transducer (with a vent hole in the oximeter housing) or a stainless steel diaphragm pressure transducer, with the diaphragm exposed to the atmosphere, can be utilized.

To test the flash reflection oximeter 10, the inventors have used relative measurements of the ratio of oxygenated hemoglobin to total hemoglobin under known physiological conditions. An occluding cuff (a blood pressure type cuff) was applied to an arm and periodic measurements distal to the cuff were made before, during and after occlusion. Before occlusion, a baseline was obtained of the measured ratio of SaO$_2$. During occlusion above systolic pressure, the measured ratio of SaO$_2$ fell below the baseline. Upon deflation of the occluding cuff, the measured ratio of SaO$_2$ returned to baseline, transiently exceeded the baseline (the expected hyperemic response), and then returned to the original baseline.

The oximeter of this invention works well through material such as standard clothing, and protective patient wraps. This is a joint function of the high intensity pulse of light, sensitive light detectors, and the porosity of these articles of clothing.

The flash reflection oximeter is not measurement site limited and measurements can be made proximal to a tourniquet or an occlusion cuff. Furthermore, in the case of intense vasoconstriction of the limbs (e.g. secondary to hypothermia) more central anatomical areas (neck, thorax, abdomen) can be used as measurement sites and differential measurements can be made. A very low reading with the oximeter at various measurement sites will confirm the absence of a pulsating vascular bed, indicating cardiac arrest or death.

The small size and weight of the oximeter is appropriate for use by medical personnel at the scene of an emergency. The ease of use and short measurement time of the oximeter reduces the workload of medical personnel. The short measurement time is appropriate for use on board a helicopter, for instance, where noise and vibration impede vital signs measurements. The high intensity, short duration flash penetrates patient clothing and protective wraps. Furthermore, the high intensity, short duration flash, with synchronization to the detection circuits, is insensitive to ambient lighting conditions. Direct application to the subject's clothing makes the oximeter insensitive to ambient humidity and smoke. Stable electronics and a rugged, lightweight housing makes the oximeter very reliable, requiring infrequent calibration.

The oximeter is unaffected by sex, age, and pigmentation. The oximeter is also unaffected by clothing and patient movement. The oximeter permits rapid measurement of $SaO_2$ in less than one second and without the need to affix sensors. The determination of percent $SaO_2$ permits determination of peripheral tissue oxygenation and thus the direct assessment of the cardiopulmonary function of a patient. Furthermore, the oximeter permits detection of tissue hypoxia, even in subjects completely encased in protective gear, and direct assessment of the degree of tissue hypoxia (from mild to life threatening).

The oximeter has other applications, such as a noninvasive input sensor for a servo-controlled low flow oxygen delivery system, which can reduce field oxygen consumption and loss while maintaining a patient normoxic. Another application is obstetrics, where (in combination with fiberoptics) the oximeter can be used in lieu of traditional, invasive fetal blood sampling for determination of fetal distress syndrome.

We claim:

1. A method of determining the oxygenation of a tissue sample by use of an apparatus having:
   a means for producing light of an intensity capable of penetrating clothing adjacent the tissue sample, such that the light is reflected by the tissue sample back through the clothing; and
   a means for responding to the reflected light and for producing an output signal related to the oxygenation of the tissue sample; the steps comprising:
   placing said apparatus adjacent clothing covering the tissue of a patient;
   producing light by operation of said means for producing light in a plurality of pulses such that the light penetrates the clothing of the patient and is reflected by the tissue back through the clothing; and
   sensing the reflected light by operation of said means for responding and producing an output signal related to the oxygenation of the tissue; and
   further comprising the step of determining the oxygenation of the tissue by comparing differences in the output signal corresponding to different pulses of produced light.

2. The method of claim 1 wherein the light is supplied in pulses of an intensity which would burn the patient if the light were not supplied in pulses.

3. The method of claim 2 wherein the pulses are at least as short as 10 microseconds.

* * * * *